(12) United States Patent
Dubi

(10) Patent No.: US 7,824,325 B2
(45) Date of Patent: Nov. 2, 2010

(54) IN VIVO FOR IMPROVING DIASTOLIC VENTRICULAR FUNCTION

(75) Inventor: Shay Dubi, Tel-Aviv (IL)

(73) Assignee: Corassist Cardiovascular Ltd., Yokneam (IL)

( * ) Notice: Subject to any disclaimer, the term of this patent is extended or adjusted under 35 U.S.C. 154(b) by 885 days.

(21) Appl. No.: 10/577,366

(22) PCT Filed: Oct. 28, 2004

(86) PCT No.: PCT/IL2004/000986

§ 371 (c)(1),
(2), (4) Date: Jan. 19, 2007

(87) PCT Pub. No.: WO2005/041745

PCT Pub. Date: May 12, 2005

(65) Prior Publication Data

US 2008/0071133 A1    Mar. 20, 2008

Related U.S. Application Data

(60) Provisional application No. 60/515,903, filed on Oct. 31, 2003.

(51) Int. Cl.
*A61N 1/362* (2006.01)
(52) U.S. Cl. .......................................... 600/16; 600/18
(58) Field of Classification Search ............. 607/16–18; 600/16–18; 623/1–11
See application file for complete search history.

(56) References Cited

U.S. PATENT DOCUMENTS 4,690,134 A * 9/1987 Snyders ..................... 601/153
5,131,905 A * 7/1992 Grooters ...................... 600/16
5,169,381 A   12/1992 Snyders
5,192,314 A * 3/1993 Daskalakis ................ 623/3.21
5,571,074 A   11/1996 Buckman, Jr. et al.
5,702,343 A * 12/1997 Alferness ..................... 600/37
5,738,627 A   4/1998 Kovacs et al.

(Continued)

FOREIGN PATENT DOCUMENTS

WO    0178625    10/2001

(Continued)

OTHER PUBLICATIONS

Colucci and Braunwald Heart Disease : Review and Assessment "Chapter 13: Pathophysiology of Heart Failure", third edition, 1997, Saunders Company Publishers, 12 pages.

(Continued)

*Primary Examiner*—Carl H Layno
*Assistant Examiner*—Paula J Stice
(74) *Attorney, Agent, or Firm*—Nixon & Vanderhye P.C.

(57) ABSTRACT

The present invention provides an anatomically-compatible and physiologically-compatible in vivo device for improving diastolic function of either the left or right ventricle of the heart, comprising at least one air-impermeable sheet that is capable of being operatively connected to the external ventricular surface of the heart using one or more connecting elements, such that said at least one air-impermeable sheet is capable of creating a sub-atmospheric pressure within said closed empty space as a consequence of changes in the volume of said space during the course of the cardiac cycle, thereby exerting an outward and normally directed force on the external ventricular surface of the heart.

12 Claims, 9 Drawing Sheets

U.S. PATENT DOCUMENTS

| | | | |
|---|---|---|---|
| 5,749,839 | A | 5/1998 | Kovacs |
| 6,592,619 | B2* | 7/2003 | Melvin ...................... 623/3.11 |
| 2002/0028981 | A1 | 3/2002 | Lau et al. |
| 2004/0002626 | A1* | 1/2004 | Feld et al. ...................... 600/37 |
| 2004/0092790 | A1* | 5/2004 | Yadav et al. .................. 600/16 |
| 2004/0267086 | A1* | 12/2004 | Anstadt et al. ................ 600/17 |

FOREIGN PATENT DOCUMENTS

| | | |
|---|---|---|
| WO | 2004066805 | 8/2004 |

OTHER PUBLICATIONS

Vasan et al., "Diastolic Heart Failure—No Time to Relax", New England Journal of Medicine 2001, vol. 344, pp. 56-59, 5 pages.

Opie, H. L. "The Heart Physiology, From Cell to Circulation", third edition, Lippincott-Raven publishers, 1998, chapter 12, pp. 343-389.

Mandinov et al., "Diastolic Heart Failure", Cardiovascular Research, vol. 54, Issue 4, Mar. 2000, pp. 813-825, 20 pages.

"How to Diagnose Diastolic Heart Failure", European Heart Journal, 1998, vol. 19, pp. 990-1003.

Gandhi et al., "The Pathogenesis of Acute Pulmonary Edema Associated with Hypertension," New England Journal of Medicine, 2001, vol. 344, pp. 17-22, 8 pages.

Sweitzer et al., "Diastolic Heart Failure: Miles to go Before We Sleep," American Journal of Medicine, 2000, vol. 109, pp. 683-685, 5 pages.

Grauer, "Heart Failure, Diastolic Dysfunction and the Role of the Family Physician," American Family Physician, 2001, vol. 63, pp. 1483-1486, 4 pages.

Philbin et al., "Systolic Versus Diastolic Heart Failure in Community Practice: Clinical Features, Outcomes, and the Use of Angiotensin-Converting Enzyme Inhibitors," American Journal of Medicine, 2000, vol. 109, pp. 605-613, 9 pages.

Morris-Thurgood et al., "Pacing in Heart Failure: Improved Ventricular Interaction in Diastole Rather Than Systolic Re-Synchronization," Europace, 2000, vol. 2, pp. 271-275.

Skinner et al, "Acute Circulatory Support by Mechanical Ventricular Assistance Following Myocardial Infarction," Journal of Thoracic and Cardiovascular Surgery, 1967, vol. 54, pp. 785-794.

Braunwald, "Heart Failure", Harrison's Principles of Internal Medicine, 14$^{th}$ Edition, McGraw Hill Publishers, Chapter 233, pp. 1287-1298.

International Search Report for PCT/IL04/00986 dated Jul. 14, 2005.

Israeli Office Action issued for Israeli Patent Application No. IL 175263, dated Aug. 11, 2010.

* cited by examiner

End Diastole　　　　End Systole

IN VIVO FOR IMPROVING DIASTOLIC VENTRICULAR FUNCTION

This application is a U.S. continuation-in-part of international application PCT/IL2004/000986 filed 28 Oct. 2004, which designated the U.S. and claims benefit of U.S. Provisional Application No. 60/515,903 filed 31 Oct. 2003, the entire contents of each of which are hereby incorporated by reference.

FIELD OF THE INVENTION

The present invention relates to a device for improving ventricular function of the heart and, more particularly, to an in vivo vacuum device for improving diastolic function of the left ventricle of the heart.

BACKGROUND OF THE INVENTION

Heart failure is commonly defined as the inability of the left ventricle, herein, also referred to as LV, to generate an adequate cardiac output at rest or during exertion, while operating at a normal or enhanced LV filling pressure. Congestive heart failure (CHF) is a clinical syndrome in which heart failure is accompanied by the symptoms and signs of pulmonary and/or peripheral congestion. Heart failure is most commonly associated with impaired LV systolic function. A widely used index for quantifying systolic function is 'ejection fraction' (EF), defined as the ratio of stroke volume to end-diastolic volume, which can be estimated using techniques such as radiocontrast, radionuclide angiography, and/or, echocardiography. The normal value of EF is $0.67 \pm 0.08$, which is frequently depressed in systolic heart failure even when the stroke volume is normal. A value of $EF \geq 0.50$ is commonly used as an indicator of normal systolic function. It is notable, however, that as much as 30-50% of all patients with typical symptoms of congestive heart failure have a normal or slightly reduced ejection fraction, that is, a value of $EF \geq 0.45$.

In these patients, diastolic dysfunction is implicated as a major contributor of congestive heart failure. In some patients, systolic and diastolic heart failure coexist.

The most common form of heart failure, the one caused by coronary arteriosclerosis, is an example of combined systolic and diastolic failure, as described in "Braunwald's Heart Disease: Review and Assessment", third edition, 1997, Saunders Company Publishers. There are about 4.6 million people in the United States with heart failure, and about 550,000 are being reported annually, as indicated by Vasan, R. S., and Benjamin, E. J., in "Diastolic Heart Failure—No Time to Relax", New England Journal of Medicine 2001, 344: 56-59. Also indicated therein, is that the mortality rate from diastolic heart failure (DHF), 5-12% annually, is about four times that among persons without heart failure and half that among patients with systolic heart failure, and that, nonetheless, rates of hospitalization and health care associated with diastolic heart failure rival those associated with systolic heart failure.

Primary diastolic dysfunction is typically observed in patients with hypertension and hypertrophic or restrictive cardiomyopathy, but can also occur in a variety of other clinical disorders and has a particularly high prevalence in the elderly population. Aging is associated with 'physiologic' diastolic dysfunction due to the increase in LV muscle mass and changes in passive elastic properties of the myocardium, hence, the concern of an increase in the incidence of diastolic dysfunction as the aging of the western world population progresses.

For the purpose of clearly understanding, and implementing, the following described preferred embodiments of the present invention, relevant details, description, and, definitions of selected terms, well known to one of ordinary skill in the art, of physiological and pathological aspects, mechanisms, and functions, of the heart, in general, and of the ventricles and atria, in particular, are provided herein. Additional details, description, and, definitions of terms, thereof, are readily available in the scientific literature.

The left ventricle is the chamber on the left side of the heart that receives oxygenated arterial blood from the left atrium and contracts to drive it into the aorta for distribution to the body. The right ventricle is the chamber on the right side of the heart that receives deoxygenated venous blood from the right atrium and drives it into the pulmonary artery in order to receive oxygen from the lungs. Diastole is the normal rhythmically occurring relaxation and dilatation (stretching, expansion, dilation) of the heart cavities (ventricles), during which the cavities are filled with blood. Atrial contraction occurs during the last stage of diastole of the ventricle and aids ventricular filling. Systole is the rhythmic contraction of the heart, especially of the ventricles, by which blood is driven through the aorta and pulmonary artery after each dilation or diastole.

Ventricular filling starts just after mitral valve opening. As the LV pressure decreases below that in the left atrium, the phase of rapid or early filling of the LV accounts for most of ventricular filling. LV filling temporarily stops as pressures in the atrium and left ventricle equalize, commonly known as the phase of diastasis, occurring prior to atrial contraction and during which little blood enters the filled left ventricle. Atrial contraction increases the pressure gradient from the atrium to the left ventricle to renew filling. When the LV fails to relax normally, as in 'LV hypertrophy', increased atrial contraction can enhance late filling. Relaxation (inactivation of contraction) is a dynamic process that begins at the termination of contraction and occurs during isovolumetric relaxation and early ventricular filling. 'Myocardial elasticity' is the change in muscle length for a given change in force. 'Ventricular compliance' is the change in ventricular volume for a given change in pressure, and, 'ventricular stiffness' is the inverse of compliance.

The 'preload' is the load present before contraction has started and is provided by the venous return that fills the ventricle during diastole. The 'Frank Starling law of the heart' states that the larger the volume of the heart, the greater the energy of its contraction and hence the stroke volume is larger. In other words, when the preload increases, the left ventricle distends (widens, expands) and the stroke volume increases, as described by Opie, H. L., in "The Heart Physiology, From Cell To Circulation", third edition, Lippincott-Raven publishers, 1998. The pressure-volume relation curves are an accepted description of the ventricular function.

FIG. 1, adapted from the previously cited "Braunwald's Heart Disease: Review and Assessment" reference, is a schematic diagram illustrating a typical pressure-volume loop of a normal subject (dotted line) and a patient with diastolic dysfunction (solid line), wherein dashed lines, between the letters 'a' and 'b', and, 'c' and 'd', represent the diastolic pressure-volume relation of the normal subject, and, the patient with diastolic dysfunction, respectively. FIG. 1 shows that isolated diastolic dysfunction is characterized by a shift in the pressure-volume loop to the left. Contractile performance is normal, associated with an ejection fraction (EF) value $\geq 0.45$, with a normal or slightly decreased stroke volume. However, LV (left ventricular) pressures throughout diastole are increased, at a common diastolic volume equal to about 70 ml/m². In the patient with diastolic failure, LV end diastolic pressure is about 25 mm Hg, compared with an LV end diastolic pressure of about 5 mm Hg in the normal subject. Thus, diastolic dysfunction increases the modulus of chamber stiffness. A main objective of treating the patient with diastolic dysfunction is to cause the diastolic pressure-volume relation curve (dashed line between 'c' and 'd') to go back to the diastolic pressure-volume relation curve (dashed line between 'a' and 'b', also indicated by the arrow), of the normal subject, by decreasing the end diastolic LV pressure for the same LV volume.

The fundamental problem in diastolic heart failure (DHF) is the inability of the left ventricle to accommodate blood volume during diastole at low filling pressures, as described by Mandinov, L., Eberli, F. R., Seiler, C., and Hess, M. O., in "Diastolic Heart Failure", Cardiovascular Res. 2000, 45: 813-825. Initially, hemodynamic changes may be manifested only in an upward displacement of the diastolic pressure-volume curve in the presence of a normal end-diastolic volume with inappropriate elevation of LV diastolic, left atrial and pulmonocapillary pressure (as previously described above, with reference to FIG. 1). More severe resistance to LV filling may cause inadequate filling even in enhanced diastolic pressure with an additional leftward shift of the diastolic pressure-volume relation, resulting in a decreased end diastolic volume and depressed stroke volume, as described by Mandinov, L., et al.

Currently, four different pathophysiological mechanisms are known and used for understanding and/or explaining diastolic heart failure (DHF), combinations of which may readily take place in a particular patient: (1) slow isovolumic left ventricular relaxation, (2) slow early left ventricular filling, (3) reduced left ventricular diastolic distensibility, and, (4) increased left ventricular chamber stiffness or increased myocardial muscle stiffness, as described in the report, "How To Diagnose Diastolic Heart Failure: European Study Group On Diastolic Heart Failure", European Heart Journal, 1998, 19: 990-1003.

Slow isovolumic left ventricular relaxation, (1), refers to a longer time interval between aortic valve closure and mitral valve opening and a lower negative peak ventricular dP/dt. Regional variation in the onset, rate, and extent of myocardial lengthening is referred to as 'diastolic asynergy'; temporal dispersion of relaxation, with some fibers commencing to lengthen later than others, is referred to as 'asynchrony'. Slow early left ventricular filling, (2), is a result of slow myocardial relaxation, segmental incoordination related to coronary artery disease and the atrioventricular pressure gradient. Reduced left ventricular diastolic distensibility, (3), refers to an upward shift of the LV pressure-volume relation on the pressure-volume plot, irrespective of a simultaneous change in slope. Reduction in LV end diastolic distensibility is usually caused by extrinsic compression of the ventricles as in cardiac tamponade. Increased LV chamber stiffness or increased myocardial muscle stiffness, (4), as manifested by a shift to a steeper ventricular pressure-volume curve, is due to processes such as ventricular hypertrophy, endomyocardial fibrosis, disorders with myocardial infiltration (for example, amyloidosis) and replacement of normal, distensible myocardium with non-distensible fibrous scar tissue in healed infarct zones.

The previously cited European Study Group proposed criteria for the diagnosis of DHF. Accordingly, simultaneous presence of the following three criteria is considered obligatory for establishing a diagnosis of DHF: (1) evidence of CHF, (2) normal or mildly abnormal LV systolic function, (3) evidence of abnormal LV relaxation, filling, diastolic distensibility, or, diastolic stiffness.

Pulmonary edema is the result of the increase in pulmocapillary pressure and is due to a shift of liquid from the intravascular compartment to the lung interstitial compartment. Pulmonary edema is frequently associated with hypertension. Gandhi, S. K. et al., in "The Pathogenesis Of Acute Pulmonary Edema Associated With Hypertension", New England Journal of Medicine, 2001, 344: 17-22, have contradicted the hypothesis that pulmonary edema, apparently associated with hypertension, in patients with preserved ejection fraction, is due to transient systolic dysfunction. They found that the LV ejection fraction and the extent of regional wall motion measured during the acute episode of hypertensive pulmonary edema were similar to those measured after the resolution of the congestion, when the blood pressure was controlled, thus concluding that the pulmonary edema was due to diastolic rather than systolic heart failure.

The management of diastolic heart failure is difficult. There have been no large-scale, randomized controlled trials of therapy in diastolic heart failure, and there remains substantial disagreement about the appropriate therapy for this disease, according to Sweitzer, N. K., and Stevenson, L. W., in "Diastolic heart Failure: Miles To Go Before We Sleep", American Journal of Medicine, 2000, 109: 683-685. Medical therapy of diastolic dysfunction is often empirical and lacks clear-cut pathophysiologic concepts, as indicated in previously cited Mandinov, L. et al. No single drug presently exists which selectively enhances myocardial relaxation without negative effects on LV contractility or pump function, and thus, there is a significant need for a new therapeutic approach for this particular type of heart disease.

Treatment of diastolic heart failure may be logically divided into three areas or categories: (1) removal of the precipitating cause, (2) correction of the underlying cause, and, (3) control of the congestive heart failure state. Treatment goals that have been advocated, by previously cited Mandinov, L. et al., and, by Braunwald, E., in "Heart Failure", Harrison's Principles of Internal Medicine, fourteenth edition, McGraw Hill publishers, are as follows:

1. Reduction of central blood volume. Reduction of salt intake and use of diuretics (usually, loop diuretics). Diuretics are effective in reducing pulmonary congestion, shifting the pressure-volume relation downwards. However, they must be used with care because the volume sensitivity of patients with diastolic dysfunction bears the risk that excessive diuresis may result in a sudden drop in stroke volume. Because of the steep pressure-volume relationship, a small decrease in diastolic volume will cause a large decrease of the filling pressure, and will result in a drop in stroke volume, and thus, in cardiac output.

2. Reduction of workload. Reduction of physical activity, maintenance of emotional rest and use of vasodilators. Vasodilators, such as sodium nitroprusside or ACE inhibitors reduce the filling pressure and the afterload in all patients, and elevate cardiac output. Reduction of an elevated left ventricular end diastolic pressure may improve subendocardial perfusion, thus improving myocardial contraction. Nonetheless, vasodilators have not been useful in the management of isolated diastolic heart failure and are more effective in combined heart failure, as indicated in the previously cited Braunwald, E. text. Vigorous control of hypertension is imperative in patients with heart failure caused by diastolic dysfunction, because control of hypertension may prevent progression or may partially reverse the disorder by addressing the primary cause of most cases, as described by Grauner, K., in "Heart Failure, Diastolic Dysfunction and the Role of the Family Physician", American Family Physician, 2001, 63: 1483-1486.

3. Improvement of LV relaxation. In particular, by using calcium channel blockers or ACE inhibitors. $Ca^{2+}$ channel blockers have been shown to improve myocardial relaxation and enhance diastolic filling. These drugs may be best matched to the pathophysiology of relaxation disturbances due to their ability to decrease cytoplasmic calcium concentration and reduce afterload. However, currently, use of $Ca^{2+}$ channel blockers is limited due to their negative inotropic effects (negative influence on the systolic function of the heart), and clinical trials have not clearly proven them to be beneficial.

4. Regression of LV hypertrophy. In particular, decrease in wall thickness and removal of excess collagen by ACE inhibitors and AT-2 antagonists or Spironolactone. Philbin, E. F., Rocco, T. A., Lindenmuth, N. W., Ulrich, K., and Jenkins, O. L., in "Systolic Versus Diastolic Heart Failure In Community Practice: Clinical Features, Outcomes, And The Use Of ACE Inhibitors", American Journal of Medicine, 2000, 109: 605-613, have shown that the use of ACE inhibitors in patients with ejection fraction equal to or greater than 0.50 was associated with a better NYHA class (New York Heart Association functional and therapeutic classification for stages of heart failure) after discharge from hospitalization, but had no significant effect on mortality or hospital readmission. ACE inhibitors and AT-2 antagonists affect blood pressure, reduce afterload, and affect the myocardium via the local renin-angiotensin system. These effects are important for regression of LV hypertrophy, and improvement of elastic properties of the myocardium.

5. Maintenance of atrial contraction and control of heart rate. In particular, by using beta-blockers and/or antiarrhythmics. Beta-blockers reduce blood pressure and myocardial hypertrophy. The positive effect on diastolic dysfunction is mainly due to slowing of the heart rate and not to a primary improvement in isovolumic relaxation or the diastolic properties of the left ventricle.

6. NO donors. NO (Nitric Oxide) donors have been shown to exert a relaxant effect on the myocardium, which is associated with a decrease in LV end diastolic pressure. In patients with severe LV hypertrophy, an increased susceptibility to NO donors has been documented, which may be beneficial for the prevention of diastolic dysfunction.

7. Heart transplantation. Heart transplantation is a definitive treatment for end stage heart failure.

8. Biventricular pacing. Biventricular pacing improves uncoordinated contraction due to left bundle branch block or other conduction abnormalities with wide 'QRS complex' (P-Q-R-S-T waveform) of an electrocardiogram, which are common in patients with CHF. Morris-Thurgood, J. A., Turner, M. S., Nightingale, A. K., Masani, N., Mumford, C., and, Frenneaux, M. P., in "Pacing In Heart Failure: Improved Ventricular Interaction In Diastole Rather Than Systolic Re-synchronization", Europace 2000, 2: 271-275, have shown that left ventricular pacing acutely benefits congestive heart failure patients with pulmonary capillary wedge pressure greater than 15 mm Hg, irrespective of left bundle branch block. They suggested the beneficial mechanism might be related to an improvement of ventricular interaction in diastole (VID) rather than ventricular systolic re-synchronization. According to their suggestion, LV pacing in patients with high LV end diastolic pressure, will delay right ventricular filling and allow greater LV filling before the onset of VID. Biventricular pacing, however, has not been clinically proven effective in the treatment of patients with diastolic heart failure.

To one of ordinary skill in the art, there is thus a need for, and it would be highly advantageous to have an in vivo device for use in improving diastolic function of the left ventricle of the heart, while minimally disturbing systolic function of the heart. Moreover, there is a need for such a device which is biocompatible and is specially configured for compact and long-term reliable use in humans.

One of the purposes of the present invention is to provide an indwelling in vivo device that may be used to improve diastolic function of either the left ventricle or right ventricle of the heart.

Another purpose of the present invention is to provide such a device that may be readily adapted to the precise topographic conformation of the heart that is to be treated.

Yet another purpose of the present invention is to provide such a device that may be readily delivered to the required site on the external surface of the ventricle by non-invasive or minimally-invasive means.

A further purpose of the present invention is to provide an in vivo device that overcomes the problems and disadvantages of previous devices.

Further objects and advantages of the present invention will become clear as the description proceeds.

SUMMARY OF THE INVENTION

The present invention relates to an in vivo device for improving diastolic function of the left or right ventricle of the heart, said device being a modification of the devices disclosed in co-pending international patent application no. PCT/IL02/00547 (published as WO 03/007778), U.S. application Ser. No. 10/353,085 and co-pending Israeli patent application no. 154141. The modified device disclosed and described herein possesses certain advantageous features over and above those recited in the corresponding inventions disclosed in the aforementioned patent applications, all of which advantages will be enumerated and described in more detail hereinbelow.

The present invention is primarily directed to an anatomically-compatible and physiologically-compatible in vivo device for improving diastolic function of either the left or right ventricle of the heart, comprising:

at least one air-impermeable sheet that is capable of being operatively connected to the external ventricular surface of the heart by means of one or more connecting elements, wherein said at least one sheet is curved or angled, such that a hollow space exists between said sheet and the imaginary surface containing the perimeter of said sheet, such that when said air-impermeable sheet is operatively connected to the external ventricular surface of the heart, a closed empty space is created between the lower surface of said sheet and said external ventricular surface, such that said at least one air-impermeable sheet is capable of creating a sub-atmospheric pressure within said closed empty space as a consequence of changes in the volume of said space during the course of the cardiac cycle, thereby exerting an outward and normally directed force on the external ventricular surface of the heart to which said air-impermeable sheet may be connected by means of said one or more connecting elements.

The term "anatomically compatible" as used hereinbefore refers to the fact that the structure of the device of the invention is such that it may readily be adapted in situ to the precise shape and size of the heart to be treated.

The term "physiologically compatible" as used hereinbefore refers to the fact that the structure of the device of the invention is such that it may readily be adapted in situ to the precise movement vectors of the heart to be treated.

The term "air-impermeable", used in connection with the aforementioned sheet, is to be understood in the sense that the material from which said sheet is formed does not permit transfer of air to the extent that the device of the invention may produce and maintain negative pressures in the order of −1 to −40 mmHg.

The term "lower surface", used in relation to the air-impermeable sheet refers to the surface that faces the ventricular wall when said sheet is operatively connected to the heart. Correspondingly, the "outer surface" is the opposite surface, that is, the surface that is closer to the external body wall, when the device is secured in its operative position.

The phrase "outward and normally directed force" refers to the fact that the forces exerted by the presently-disclosed device on the external ventricular wall are, at any given point on said ventricular wall, directed at an angle of approximately 90° away from the heart (i.e. in the direction of the body wall).

Although the at least one air-impermeable sheet of the in vivo device of the invention may be constructed of any suitable material possessing the desired physical properties, in a preferred embodiment, said at least one air-impermeable sheet is constructed from biocompatible plastic or polymer. Suitable biocompatible plastics include materials such as, for example, polyethylene, homopolymers and copolymers of vinyl acetate such as ethylene vinyl acetate copolymer, polyvinylchlorides, homopolymers and copolymers of acrylates such as polymethylmethacrylate, polyethylmethacrylate, polymethacrylate, ethylene glycol dimethacrylate, ethylene dimethacrylate and hydroxymethyl methacrylate, polyurethanes, polyvinylpyrrolidone, polyacrylonitrile butadiene, polycarbonates, polyamides, fluoropolymers such as homopolymers and copolymers of polytetrafluoroethylene and polyvinyl fluoride, polystyrenes, homopolymers and copolymers of styrene acrylonitrile, cellulose acetate, homopolymers and copolymers of acrylonitrile butadiene styrene, polymethylpentene, polysulfones, polyesters, polyimides, and other similar compounds known to those skilled in the art. It should be understood that these possible biocompatible polymers are included above for exemplary purposes and should not be construed as limiting.

The device can also contain materials selected from the group consisting of tungsten, platinum, titanium, nitinol alloy, stainless steel alloy, and, combinations thereof.

In a particularly preferred embodiment, the device of the present invention is constructed of biocompatible silicon.

In one preferred embodiment of the device of the invention, said device further comprises means for the unidirectional passage of fluids and solid particles (such as cell debris) from the region of the lower surface of the air-impermeable sheet (i.e., the surface facing the external cardiac wall) to the region of the upper surface of said sheet. In one preferred embodiment of the device of the invention, said means comprise one or more one-way valves inserted into the air-impermeable sheet. Preferably, one or more tubes or shunts are connected to the inlet and outlet of each of said valves.

According to one preferred embodiment of the device of the invention, said device is constructed such that the maximal value for the normally-outward expansive pressure exerted on at least one part of the external ventricular wall is in a range of about 5 mm Hg to about 40 mm Hg.

In another aspect, the present invention is also directed to a method for improving diastolic function of either the left or right ventricle of the heart, comprising
   attaching an air-impermeable sheet to the external surface of the left ventricle, right ventricle or both ventricles,
   ascertaining that air-tight sealing of the peripheral margin of said sheet to the external ventricular wall has occurred, and optionally, as required,
   draining fluid and solid debris from the space formed between one surface of said sheet and the external ventricular wall through drainage means fitted in said sheet to a region located on the other side of said sheet.

Preferably, the air-impermeable sheet is attached to the ventricular surface during end diastole, when the ventricle is full dilated.

The presently-disclosed air-impermeable sheet may be attached to the external ventricular surface by any convenient method, including (but not restricted to) the use of biocompatible pins (including intramural and other non-transmural pins), biocompatible needles, biocompatible spikes, biocompatible screws, biocompatible clamps, biocompatible glue, surgical sutures, and, combinations thereof.

In one preferred embodiment, the connecting element is provided in the form of cardiac anchors, as described in co-owned, co-pending international patent applications PCT/IL02/00547 (published as WO 03/007778) and PCTI/IL04/000072 (published as WO 04/066805), incorporated herein by reference.

In a further preferred embodiment of the invention, attachment of the device of the invention to the external cardiac surface may be achieved using the fabric patch girdle system disclosed in co-pending Israeli patent application no. 154141, and international patent application no. PCTI/IL04/000072 (published as WO 04/066805), both of which are incorporated herein by reference.

In a further preferred embodiment of the invention, attachment of the device of the invention to the external cardiac surface may be achieved using the helical coil spring system, disclosed in co-pending, co-owned PCT/IL04/000072 (published as WO 04/066805), incorporated herein by reference.

In yet another preferred embodiment, the connecting element is provided in the form of a tube constructed of a biocompatible material. In one particularly preferred embodiment, this material is Dacron. In another particularly preferred embodiment, the material is polytetrafluorethylene (PTFE).

In one preferred embodiment of the invention, the sealing of the peripheral margin of the device to the external ventricular wall may be achieved passively, immediately following attachment of the device to the heart (by use of a suitable attachment means, as described hereinabove), following the close apposition of said margin to the cardiac tissue.

In another preferred embodiment of the method of the invention, sealing of the peripheral margin of the device to the cardiac wall occurs passively, several hours or days following attachment of the device, by virtue of the deposition of fibrotic cells and collagen in the space between said peripheral margin and the external ventricular wall.

According to one preferred embodiment of the method of the invention, the aforementioned device is constructed such that the maximal value for the normally-outward expansive pressure exerted on at least one part of the external ventricular wall is in a range of about 5 mm Hg to about 40 mm Hg.

As mentioned hereinabove, the in vivo device according to the present invention possesses a number of further significant advantageous properties in addition to those described in relation to the devices disclosed in co-pending international patent application no. PCT/IL02/00547 (published as WO 03/007778), U.S. application Ser. No. 10/353,085 and co-pending Israeli patent application no. 154141. Among these advantages are included the following desirable properties:
  a) greater anatomical compatibility of the presently-disclosed device with the ventricle of the heart to which said device is attached;
  b) greater physiological compatibility of the presently-disclosed device with the movement of the ventricle of the heart to which said device is attached;
  c) improved distribution of the force applied by the device.
  d) easier application of the device on the cardiac surface.
  e) increased range of forces and/or pressures attainable with a single device;
  f) increased range of ventricular sizes that may be accommodated with a single device;
  g) greater ease of construction of the device; and
  h) significantly lower cost of construction of the device.

Further properties and advantages of the presently-claimed device will become apparent as the description proceeds.

BRIEF DESCRIPTION OF THE DRAWINGS

The invention is herein described, by way of example only, with reference to the accompanying drawings. With specific reference now to the drawings in detail, it is stressed that the particulars shown are by way of example and for purposes of illustrative discussion of the preferred embodiments of the present invention only, and are presented in the cause of providing what is believed to be the most useful and readily understood description of the principles and conceptual aspects of the invention.

DESCRIPTION OF THE PREFERRED EMBODIMENTS

The present invention relates to an in vivo device for improving diastolic function of the left or right ventricle of the heart.

It is to be noted that the terms "ventricular", "ventricular surface", "ventricle" and the like are used herein to refer to either the left or right ventricles or to portions thereof. Thus, wherever the description refers to the left ventricle or portions thereof, it is to be appreciated that the teachings derived from said description apply equally to the right ventricle.

A key advantage possessed by all embodiments of the presently claimed in vivo device is the fact that said device is capable of exerting forces on the external ventricular wall in a Normal direction, distributed evenly throughout the entire ventricular surface to which the device is applied on. These evenly distributed Normal forces are of importance for the following two reasons:
  1. The even distribution of forces across the left ventricular wall surface assures even and symmetric movement of the ventricle, without disturbance to the twisting motion of the ventricle;
  2. Due to the even and highly spread distribution of forces, the local stress applied on the contact surface of the ventricle is reduced, thus significantly reducing the danger of local ischemia and of ventricular wall rupture.

Figure 1:
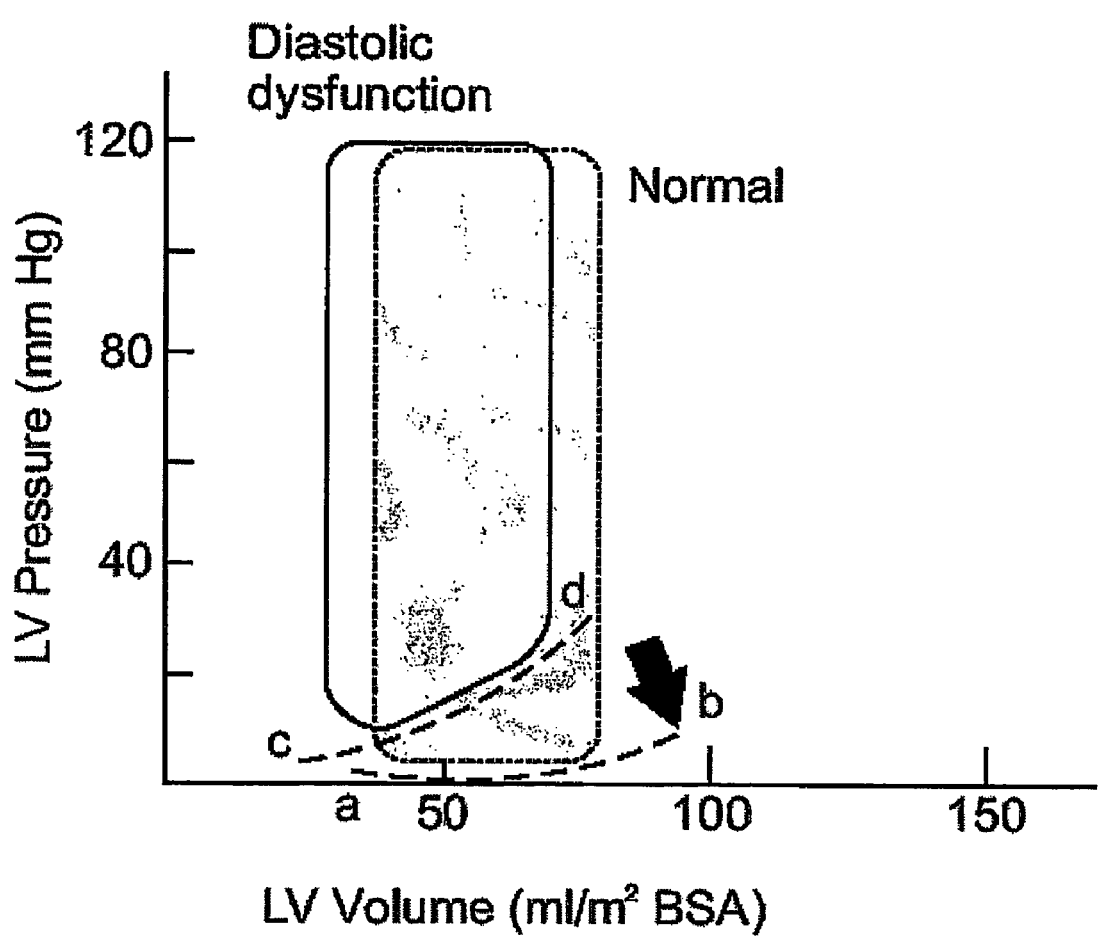
FIG. 1 is a schematic diagram illustrating a typical pressure-volume loop of a normal subject and a patient with diastolic dysfunction.

Referring now to FIG. 1, a main objective of treating a patient with diastolic dysfunction is to cause their abnormal diastolic pressure-volume relation curve (dashed line between 'c' and 'd') to go back to the diastolic pressure-volume relation curve of a normal subject, (dashed line between 'a' and 'b'), by decreasing the diastolic LV pressure for the same LV volume, during the entire diastolic stage of the cardiac cycle, in general, and, by decreasing the end diastolic LV pressure for the same LV volume (indicated by the arrow), in particular. The present invention accomplishes this.

The device of the present invention is based on uniquely applying a Normally directed, outward expansive force or pressure (force per unit area), which is evenly distributed on the wall region of the left ventricle, in order to reduce the intraluminal hydrostatic pressure of the left ventricle, also known as LV filling pressure, during the ventricular diastolic stage of the cardiac cycle, thereby, improving diastolic function of the left ventricle of the heart, while minimally disturbing systolic function of the heart.

Reduction of hydrostatic pressure within the left ventricle has the beneficial effect of reducing hydrostatic pressure in other cardiac compartments and organs preceding, that is, upstream relative to, the left ventricle in the overall cardiac system, in particular, in the left atrium, and in the pulmonary vasculature of the venous system supplying blood to the atrium. These beneficial effects prevent both dilatation of the atria with propagation to atrial fibrillation, and pulmonary congestion causing symptoms of dyspnea and pulmonary edema.

Normal left ventricular end diastolic pressure (LVEDP) is in the range of about 6-12 mm Hg, and the upper end of this range can increase to above 35 mm Hg during conditions of heart failure involving diastolic dysfunction, as a direct result of the left ventricle needing relatively high hydrostatic filling pressures in order to achieve the necessary left ventricular end diastolic volume (LVEDV) for an appropriate cardiac output.

Accordingly, an important objective of the present invention is to significantly reduce the hydrostatic pressure in the left ventricle during the diastolic stage of the cardiac cycle, thereby, improving diastolic function of the left ventricle of the heart, while minimally disturbing systolic function of the heart. In particular, fulfilling this objective includes sufficiently reducing left ventricular end diastolic pressure (LVEDP), preferably, down to the normal range of about 6-12 mm Hg, during ventricular diastole of the heart.

In addition to the present invention primarily applied for treating subjects having symptoms of diastolic heart failure, by reducing intraluminal hydrostatic pressure (LV filling pressure) of the left ventricle during the ventricular diastolic stage of the cardiac cycle, thereby, improving diastolic function of the left ventricle of the heart, while minimally disturbing systolic function of the heart, the present invention can be used in a variety of other cardiac related and/or non-related monitoring applications, such as pressure measurement applications, and, therapeutic applications, such as in drug delivery applications. For example, the device of the present invention can be used together with an apparatus for time controlled drug delivery or release to the body, in general, and, to the cardiac region, in particular.

The component parts, operation, and implementation of an anatomically compatible and physiologically compatible in vivo device for improving diastolic function of the left ventricle of the heart according to the present invention are better understood with reference to the following description and accompanying drawings. Throughout the following description and accompanying drawings, like reference numbers refer to like elements.

The device of the present invention utilizes the physicochemical property and behavior of elasticity or resiliency, and the physical properties of vacuum, in a relatively simple manner, in appropriately constructed and configured elastic or resilient components of the device operatively connected to the external surface of a wall region of the left ventricle, for exerting a negative pressure or sub-atmospheric pressure type of expansive force or pressure to the wall region of the left ventricle, for reducing intracardiac hydrostatic pressure during ventricular diastole of the heart, thereby, improving diastolic function of the left ventricle of the heart, while minimally disturbing systolic function of the heart.

Figure 5:
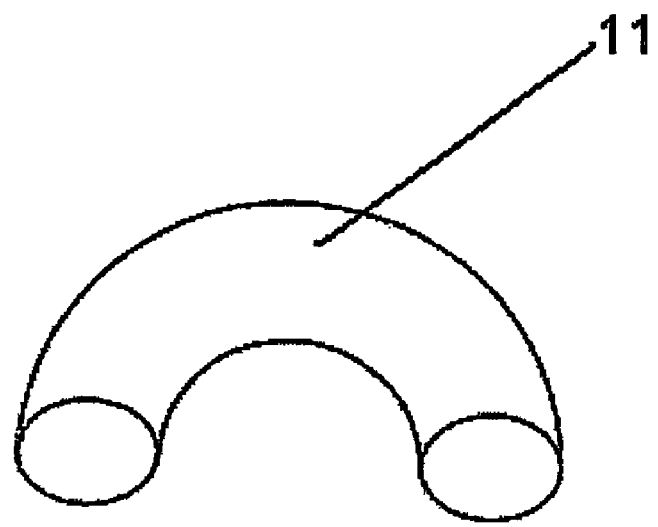
FIG. 5 is an illustration of the base of the device of the invention, which is the part attaching to the ventricular surface.
Figure 5:
Figure 5:
Figure 5:

In order to achieve a negative or sub-atmospheric pressure, the contact surface between the device and the cardiac surface needs to be sealed, or partially sealed, to prevent loss of pressure. There are several options to be considered for this sealing:

1—Acute or immediate sealing: this is achieved by characteristics of the attachment surface of the device, which when compressed against the ventricular surface, and adhered to the ventricular surface, completely separates and insulates the internal volume of space between the device and the ventricular surface from the space external to the device (the thoracic cavity). An exemplary illustration of this is shown on FIG. 5, showing that during connection of the device the base is constricted and forms a seal.

2—Chronic or late sealing: this is achieved by utilizing the physiology of a reaction to a foreign body. After attachment of the device to the ventricle, during the next days and weeks, a tissue consisting of fibrotic cells and collagen deposits is formed in the area. This tissue forms a natural, gradually forming, sealant.

Figure 4:
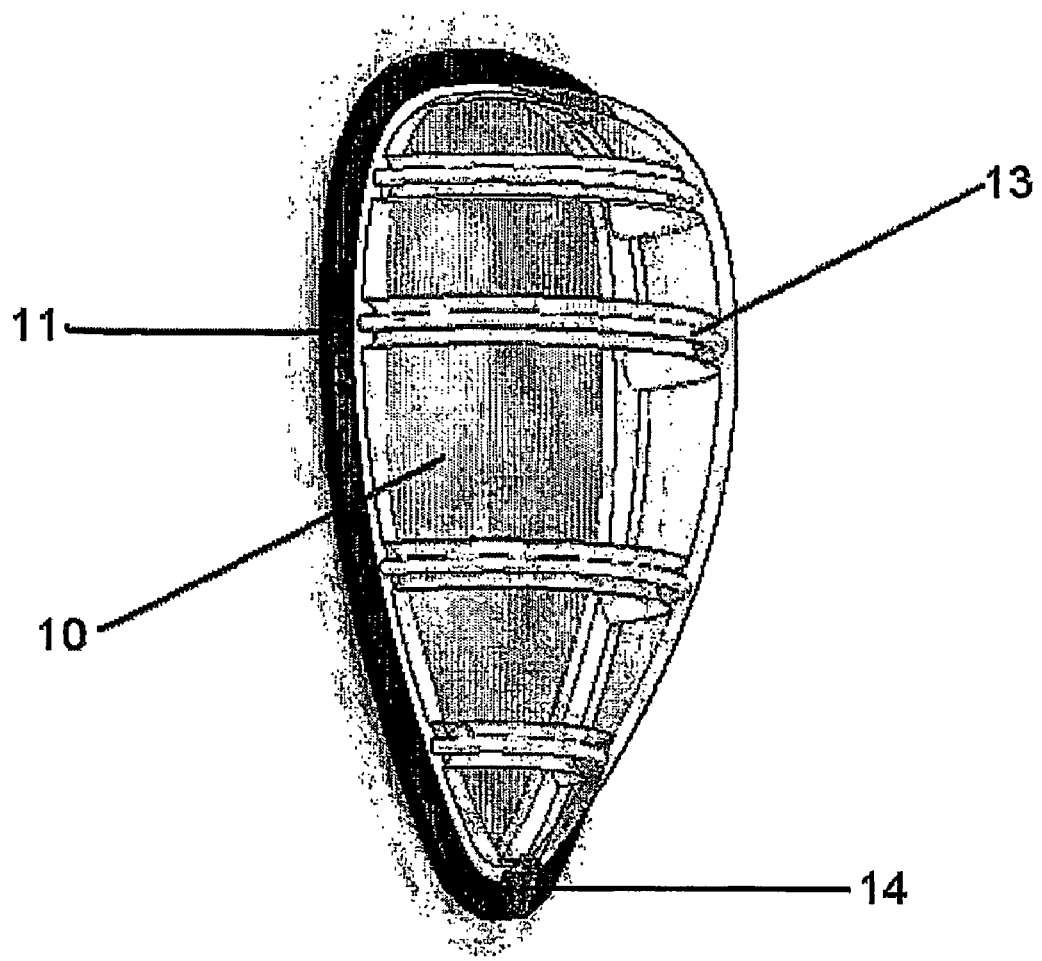
FIG. 4 is an illustration of a different angle of view of the device of the invention depicted in FIG. 3. The side facing the chest wall is demonstrated.

With time, the volume of space between the device and the ventricular surface may fill with fluid which can diffuse into this space from the ventricular cells, due to the negative pressure formed by the device. This leakage of fluid will eventually fill the space and impair the function of the device if not prevented. This can be prevented in several ways:

1—Adding a one-way valve to the device, as illustrated in FIG. 4, element 14. Through this valve the fluid will be expelled from the space into the thoracic cavity, thus preventing its accumulation and assuring continued function of the device.

2—Adding a tube or shunt with a one-way valve, which will expel the fluid from the internal space to an alternative space which may be, for example, the peritoneal space, the pleural space, the subcutaneous space, or even to a reservoir outside of the body. The externalization of fluid will prevent its accumulation and assure continued function of the device.

3—If the seal between the device base and the ventricular surface is semi-penetrable then during diastole, when the ventricle expands, the fluid within the space will be ejected out to the thoracic cavity, thus preventing accumulation of fluid.

The ventricular device of the present invention may be constructed from either a single type of material, or, from a plurality of different types of materials. Preferably, the ventricular device is constructed from a single type of material. For example, such material is selected from the group consisting of biocompatible plastic or elastomer. The device can also contain a pure metal, a metal alloy, and, combinations thereof. Exemplary pure metals are tungsten, platinum, and, titanium. Exemplary metal alloys are nitinol, and, stainless steel.

The ventricular device of the present invention has dimensions of length, height, and, width, depth, or thickness, each on the order of microns to centimeters, in the range of between about 10 microns to about 8 cm.

The geometry, shape, form, dimensions, and elastic strength, of the ventricular device, are specifically determined, in part, according to the desired or necessary physical properties, for properly and optimally performing the critical function of potentially exerting an evenly distributed Normally directed force or pressure (in a range of about 5-40 mm Hg, preferably, about 10 mm Hg) to the outer wall surface of the left ventricle, in order to properly fulfill the main objective of sufficiently reducing intracardiac hydrostatic pressure during ventricular diastole of the heart, thereby, improving diastolic function of the left ventricle of the heart, while minimally disturbing systolic function of the heart. This includes sufficiently reducing left ventricular end diastolic pressure (LVEDP), preferably, down to the normal range of about 6-12 mm Hg, during ventricular diastole of the heart.

Following are description and accompanying drawings for describing and illustrating, respectively, various embodiments of the device of the present invention.

Figure 2:
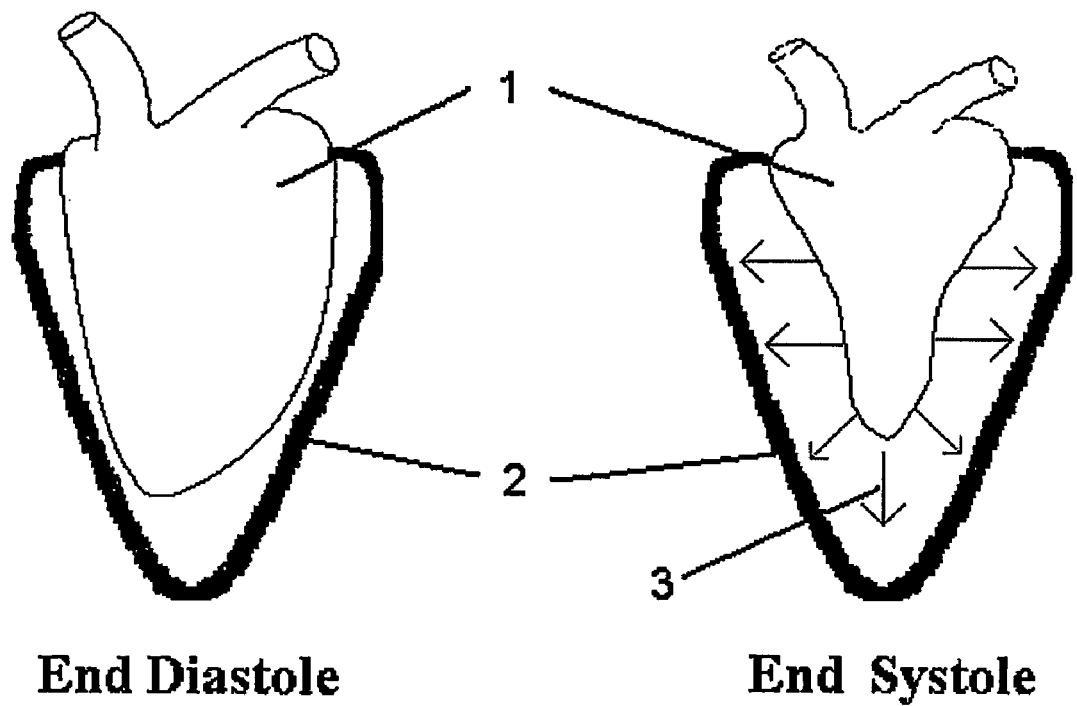
FIG. 2 depicts the general concept of the in vivo device of the invention, in which said device comprises a surface above the external ventricular wall, encompassing a volume of space. The directions of the forces acting on the ventricular wall, due to the change in volume encompassed by the device during the cardiac cycle, are illustrated.

Referring again to the drawings, FIG. 2 depicts the general concept of the in vivo device of the invention, in which said device comprises a surface above the external ventricular wall, encompassing a volume of space. The device can cover the left ventricle only, the right ventricle only, or both ventricles. The directions of the forces acting on the ventricular wall, due to the change in volume encompassed by the device during the cardiac cycle, are illustrated. The forces are generated due to the following physical principle:

Under a constant temperature, the value of P*V is constant, wherein P represents the pressure and V represents the volume. During systolic contraction of the ventricle, the volume of the internal space, between the device and the ventricular surface, enlarges. Since P*V is constant, when V enlarges, P decreases, thus creating normally directed forces, or a negative pressure. In FIG. 2, a rigid or semi-rigid or elastic cup 2 is connected to the external cardiac wall 1, and the attachment to the cardiac base is sealed to prevent loss of pressure. When the heart contracts a low pressure is created in the space between the cardiac wall and the cup, and this pressure assists with the diastolic (dilatation) movement of the heart. Optionally, the cup may be connected to an external elastic element (for example a rubber balloon), which can be located in another cavity, for example the thoracic cavity, the peritoneal space, the subcutaneous tissues or external to the body. These elements' elasticity will determine the pressure applied by the device.

Figure 3:
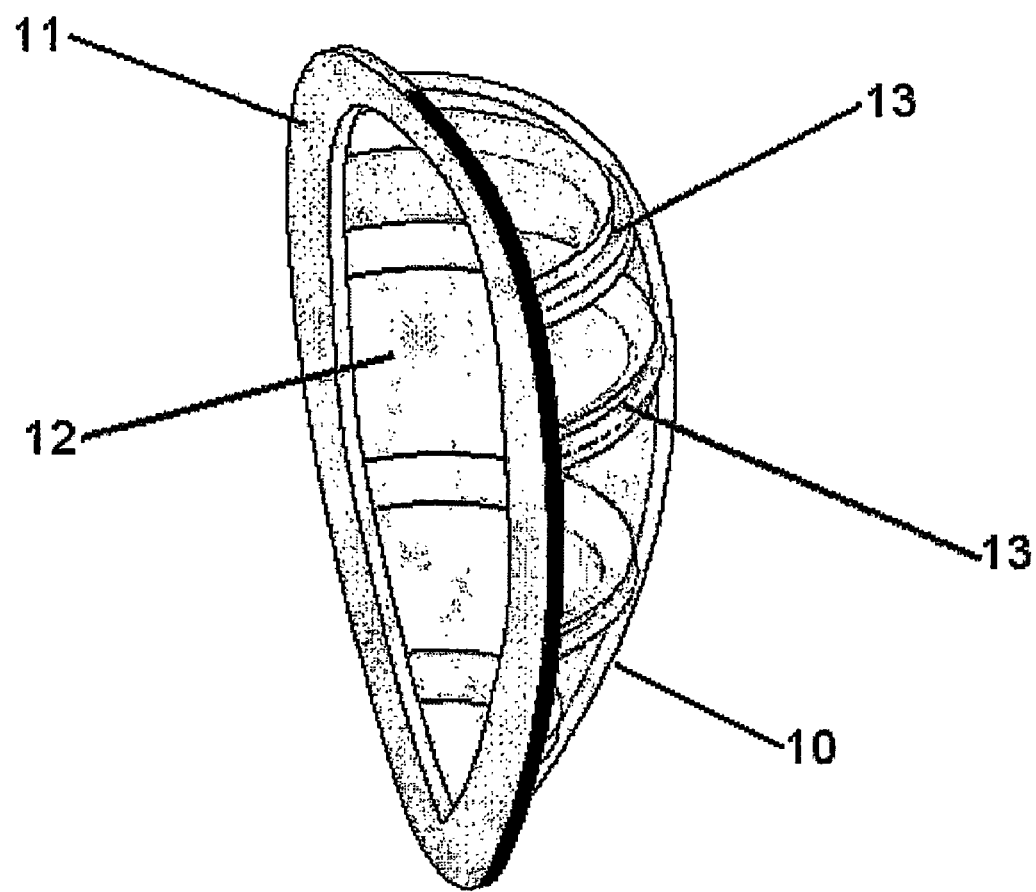
FIG. 3 depicts a preferred embodiment of the in vivo device of the invention, in which said device comprises a convex surface above the external ventricular wall, encompassing a volume of space. In this view the side facing the ventricular surface is demonstrated.

Referring again to the drawings, FIG. 3 depicts one preferred embodiment of the device of the present invention, generally indicated by numeral 10. The device is a convex shaped rigid or semi-rigid or elastic element, on which there are several rigidity-determining elements 13. The rigidity-determining elements 13 may be created by forming hollow tubes within the wall of the device, and these tubes may be filled by a rigidity-determining material, such as an elastic metal wire, a fluid, a gas or any other material determined as suitable for the functionality of the device. In FIG. 3 the rigidity-determining elements 13 are illustrated as horizontal, but this is only an example and they may be longitudinal. The filling of the rigidity-determining elements 13 may be done before performing the surgical procedure, during the procedure, or may be done at a time after the procedure, for example 2 weeks after the surgery, when the fibrotic tissue seals the attachment between the device and the ventricle. Filling the rigidity-determining elements 13 after the surgery may be done by leaving a tube connected to these elements within a body space and entering it later, or by leaving a tube connecting to an element external to the body. The device 10 is attached to the external ventricular surface via the base of the device 11. The base 11 is applied on the ventricular surface, and attached to it by the use of any suitable conventional material or means, including (but not restricted to) biocompatible pins, biocompatible needles, biocompatible spikes, biocompatible screws, biocompatible clamps, biocompatible glue, biocompatible adhesion, surgical sutures, and, combinations thereof, having dimensions of length, height, and, width, depth, or thickness, each on the order of microns to centimeters, in the range of between about 10 microns to about 8 cm. The internal side of the device, facing the ventricular surface is showed as element 12, this element encompasses a volume of space between the device and the ventricular surface.

Referring again to the drawings, FIG. 4 depicts another view of the device 10 of FIG. 3, showing the side of the device facing the thoracic cavity. The base of the device is shown as element 11, and the rigidity-determining elements 13 are shown. A valve 14 is illustrated, through which any accumulated fluid can be expelled from the space into the thoracic cavity, thus preventing its accumulation and assuring continued function of the device. In FIG. 4 there is only one valve 14 illustrated, but there can also be no valves or two or more valves. The valve 14 may be a one-way valve, allowing fluid to exit the space, but not allowing fluid to enter the space. Additionally, a tube or shunt may be connected to the valve, which may thus expel the fluid from the internal space to an alternative space which may be, for example, the peritoneal space, the pleural space, the subcutaneous space, or even to a reservoir outside of the body. The externalization of fluid will prevent its accumulation and assure continued function of the device.

The embodiments of the device depicted in FIGS. 3 and 4 may be constructed of any suitable air-impermeable material. Preferably, said embodiments are constructed of a biocompatible plastic or elastomer. Suitable biocompatible plastics include materials such as, for example, polyethylene, homopolymers and copolymers of vinyl acetate such as ethylene vinyl acetate copolymer, polyvinylchlorides, homopolymers and copolymers of acrylates such as polymethylmethacrylate, polyethylmethacrylate, polymethacrylate, ethylene glycol dimethacrylate, ethylene dimethacrylate and hydroxymethyl methacrylate, polyurethanes, polyvinylpyrrolidone, polyacrylonitrile butadiene, polycarbonates, polyamides, fluoropolymers such as homopolymers and copolymers of polytetrafluoroethylene and polyvinyl fluoride, polystyrenes, homopolymers and copolymers of styrene acrylonitrile, cellulose acetate, homopolymers and copolymers of acrylonitrile butadiene styrene, polymethylpentene, polysulfones, polyesters, polyimides, and other similar compounds known to those skilled in the art. It should be understood that these possible biocompatible polymers are included above for exemplary purposes and should not be construed as limiting.

The device may also contain metals. Examples of metals possessing the required physical properties include (but are not limited to) stainless steel 316 and NITINOL (Nickel Titanium), both of which are biocompatible metals that are commercially available in the form of wires or tubes. For example, wires of both materials may be obtained from Allvac Inc., Monroe, N.C.

Exemplary dimensions of the embodiments of the device depicted in FIGS. 3 and 4 are as follows: Longitudinal length, (that is, the length extending along imaginary central longitudinal axis) is in the range of between about 0.5 cm to about 10.0 cm, preferably, about 6 cm. The horizontal length is in the range of between about 0.1 cm and about 8.0 cm, preferably, about 5 cm. The average depth or thickness of the plastic is in the range of between about 0.01 mm (10 microns) to about 5.0 mm (5000 microns), preferably, about 0.3 mm (300 microns).

The presently-discussed embodiments, illustrated in FIGS. 3 and 4 may be manufactured by molding the material into a suitable mold.

The embodiments of the device of the invention described hereinabove and depicted in FIGS. 3 and 4 may be inserted in place using a minimally invasive surgical procedure, such as a thoracoscopy, or, thoracotomy, with a relatively small diameter delivery system for delivering and deploying the ventricular device into the body, in general, and to a left ventricular cardiac outer wall surface, in particular.

Preferably, the device 10 is self-expanding, in order to facilitate the use of minimally invasive insertion procedures such as those described above.

Techniques and equipment of thoracoscopy deployment are well taught about in the prior art.

FIG. 5 illustrates the base 11 of the device, shown also as element 11 in FIGS. 3 and 4. FIGS. 5B, 5C and 5D exemplify the change in shape of the base during the approximation of the device to the ventricular surface and the attachment of the device. The base 11 of the device can be made from any suitable biocompatible material. Preferred examples of such materials include Dacron and polytetrafluorethylene (PTFE), both of which possess the required mechanical strength and elasticity in order to function as connecting means, and may be woven into meshes. Preferably, the base tubes have an internal diameter in the range of 0.2-2 cm. Suitable Dacron tubes originally intended for use as arterial grafts are highly suitable for this purpose, and may be commercially obtained from C. R. Bard, Inc., Murray Hill, N.J., USA. FIG. 5 illustrates a type of base which acts as an immediate sealing element. The sealing is formed due to the complete adherence between the ventricular surface and the device, formed by the base of the device. The sealing enables the normally directed forces, or negative pressure, or vacuum, to be created immediately after application of the device to the external ventricular surface.

The device is attached to the ventricle during end diastole, when the ventricle is fully dilated, and there is a space between the ventricle and the device, which is sealed from the thoracic cavity. This space has zero pressure and a certain volume. During ventricular contraction (systole) the volume of this said space enlarges, and due to the fact that P*V is constant under a constant temperature (P=Pressure, V=Volume), the pressure is reduced and becomes negative. The negative pressure in the space causes a normally directed out-ward force on the ventricle.

Figure 6:
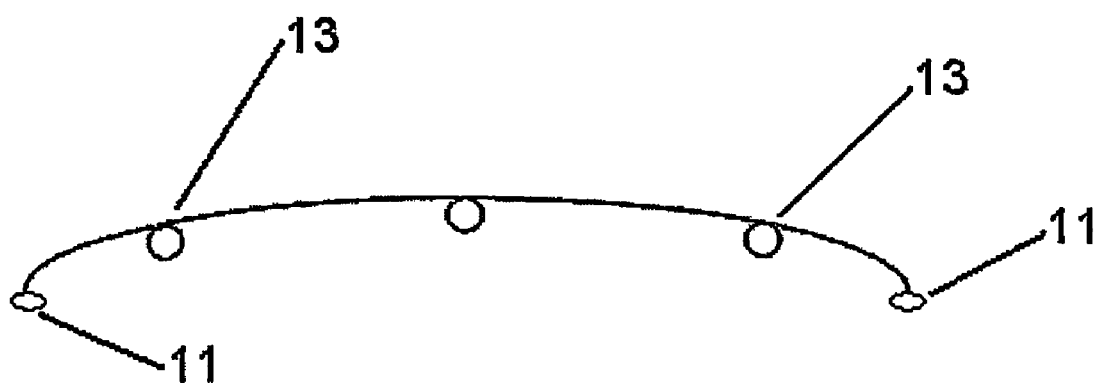
FIG. 6 is a side view of the device of the invention.

FIG. 6 depicts a side view of the device shown in FIGS. 3 and 4, illustrating the rigidity-determining elements 13 and the base 11.

Figure 7:
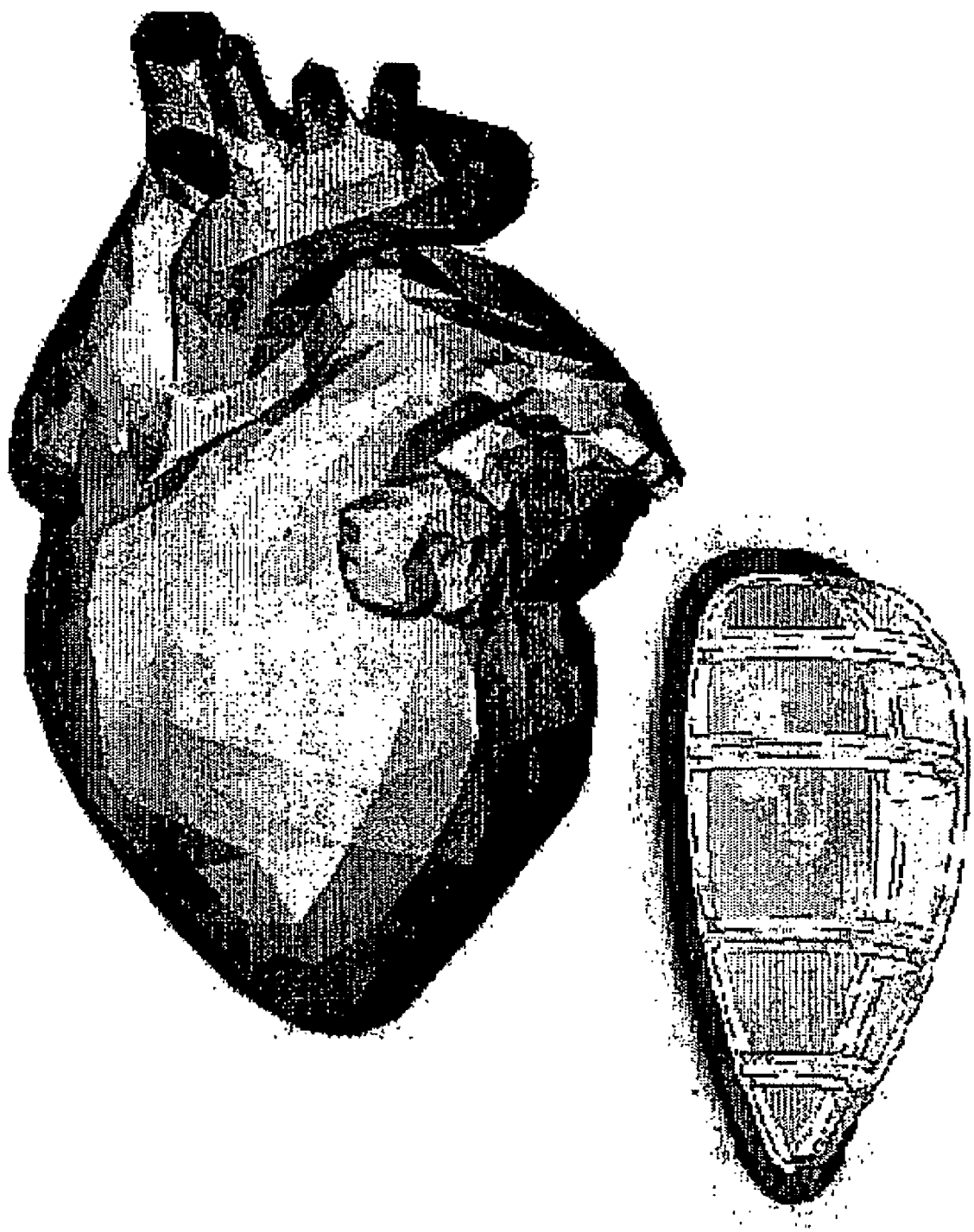
FIG. 7 depicts the device illustrated in FIG. 3 approximated to its in situ position on the external surface of the left ventricle.

FIG. 7 depicts an embodiment of the device described hereinabove (and shown in FIGS. 3 and 4) approximated to its in situ position on the external surface of the left ventricle.

The device may be connected or attached to the external surface of the heart by the use of any suitable conventional material or means, including (but not restricted to) biocompatible pins, biocompatible needles, biocompatible spikes, biocompatible screws, biocompatible helical coils, biocompatible clamps, biocompatible glue, biocompatible adhesion, surgical sutures, and, combinations thereof, having dimensions of length, height, and, width, depth, or thickness, each on the order of microns to centimeters, in the range of between about 10 microns to about 8 cm.

Figure 8:
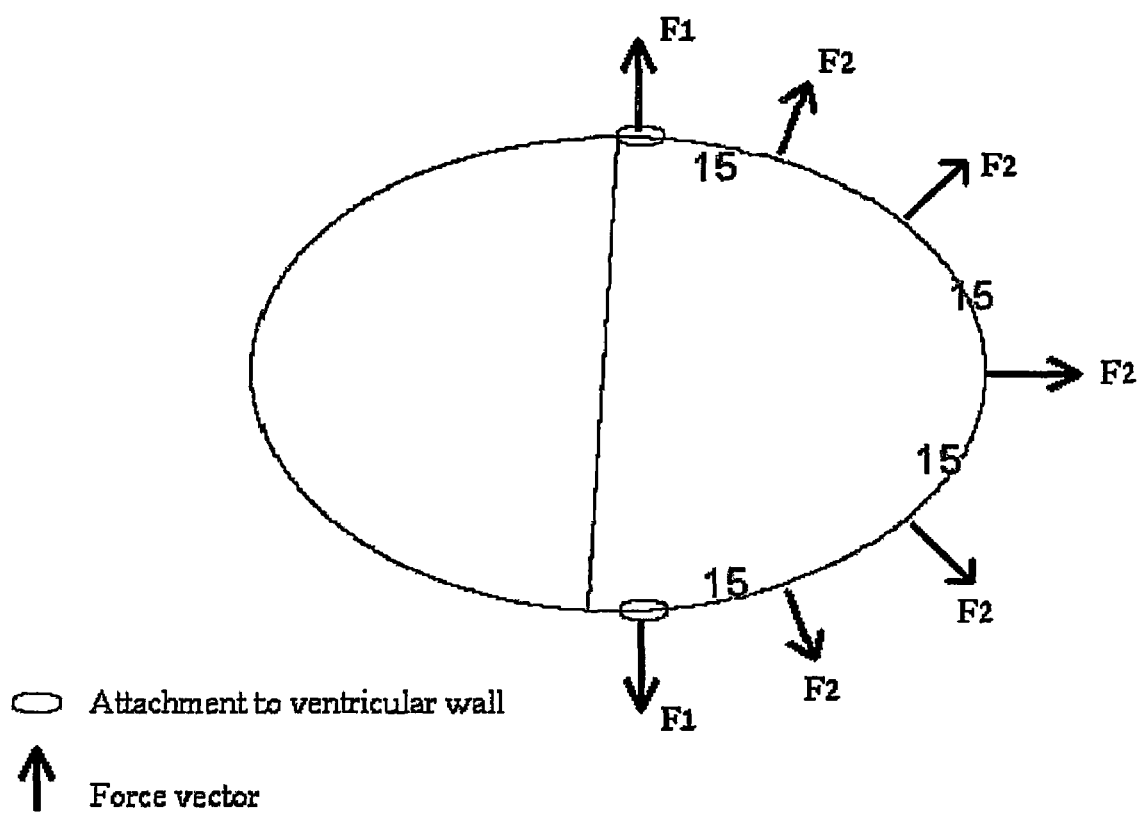
FIG. 8 schematically illustrates the direction of the forces exerted by a device of the invention on the ventricular wall.

FIG. 8 is an illustrative plan view of the heart showing the direction of the forces exerted by the device illustrated in FIG. 7 on the external surface of the left ventricular wall 15. The arrows labeled as F1 indicate the direction of the radial forces acting on the attachment points of the device to the ventricular wall 15 (shown as flattened ellipses). The arrows labeled as F2 indicate the Normally-directed forces acting on the ventricular wall 15 after attachment of the device. It will be seen from this figure that the vector sum of the forces is in a direction that will lead to an outward expansive (i.e. inflating) movement of the left ventricular wall, thus assisting the diastolic movement of the left ventricle.

Deployment of the device may be performed in the following manner: The heart is surgically exposed following midline sternotomy and pericardiotomy. The heart is then measured in various dimensions (apex to base, circumference at base and midway between base and apex) in order to assist with selection of an in vivo device of an appropriate size. The device may then be attached to the external ventricular wall by means of screwing helical coils, pinning, gluing or suturing. In the latter case, the device is sutured to the myocardium using multiple partial-thickness (deep) interrupted stitches, taking care not to compromise any of the epicardial coronary arteries. Following attachment of the device, the heart is observed in order to ascertain that detachment of the device from the myocardium has not occurred at any point. Final fixation of the device within the girdle, if needed, is now performed using interrupted stitches.

The device may also be connected to the heart by an anchoring mechanism, for example the anchors described in co-pending U.S. application Ser. No. 10/353,085, incorporated herein by reference. An advantage of the cardiac anchors described in these applications is the fact that, due to their small size and elongated shape, they may be easily inserted into an endoscopic delivery mechanism, thus enabling the insertion of the in vivo device of the invention by use of minimally-invasive methods. Attachment of the device to the external ventricular surface may also be achieved by use of the thin fabric patch girdle system disclosed in copending Israeli patent application no. 154141, incorporated herein by reference.

The following non-limiting working example illustrates the insertion and use of the in vivo device of the present invention in a healthy mammalian subject.

EXAMPLE

In Vivo Demonstration of the Implantation and Use of a Device of the Present Invention in a Mammalian Subject Anesthesia and Instrumentation:

A healthy sheep, (12 month, 38 Kg) was anesthetized (induction with xylazine+ketamine+valium; intubation and maintenance of anesthesia with enflurane; monitoring with ECG and saturation). A left thoracotomy incision was made and the chest was entered through the $5^{th}$ intercostal space. The pericardium was opened widely to allow access to the left ventricle.

Device Attachment:

The device was attached to the external ventricular wall by means of surgical suturing, using multiple partial-thickness (deep) interrupted stitches, taking care not to compromise any of the epicardial coronary arteries. The device studied in this exemplary experiment was an oval shaped silicon device (FIG. 9), with a longitudinal diameter of about 6 cm and a horizontal diameter of about 4 cm.

Figure 9:
FIG. 9 is a photographic representation of an in-vivo device that incorporates a convex silicon design as the negative pressure forming element and that has been attached to the left ventricle of a sheep by means of surgical sutures.

FIG. 9 is a photograph demonstrating a prototype of the device 20 attached to the left ventricular wall 21.

While the invention has been described in conjunction with specific embodiments and examples thereof, it is evident that many alternatives, modifications and variations will be apparent to those skilled in the art. Accordingly, it is intended to embrace all such alternatives, modifications and variations that fall within the spirit and broad scope of the appended claims.

The invention claimed is:

1. An anatomically-compatible and physiologically-compatible in vivo device for improving diastolic function of either a left or right ventricle of a heart, comprising:
at least one air-impermeable sheet that is capable of being operatively connected to an external ventricular surface of the heart by means of one or more connecting elements, wherein said at least one sheet is curved or angled to encompass a volume of space,
such that when said air-impermeable sheet is operatively connected to said external ventricular surface of the heart, the air-impermeable sheet and the ventricular surface of the heart are sealed along a peripheral margin of the sheet, and a closed empty space is created between a lower surface of said sheet and said external ventricular surface;
such that said at least one air-impermeable sheet is capable of creating a sub-atmospheric pressure within said closed empty space as a consequence of changes in the volume of said space during a course of a cardiac cycle of said heart, thereby exerting an outward and normally directed force on said external ventricular surface of the heart to which said air-impermeable sheet may be connected by means of said one or more connecting elements.

2. The device according to claim 1, wherein the air-impermeable sheet comprises a curved sheet of a biocompatible polymeric material.

3. The device according to claim 1, further comprising at least one rigidity-determining element.

4. The device according to claim 3, wherein the air-impermeable sheet is in the form of a convex shaped rigid, semi-rigid or elastic element, in which are present a plurality of laterally-disposed rigidity-determining elements.

5. The device according to claim 1, wherein said device further comprises a one-way valve inserted into the air-permeable sheet.

6. A method for improving diastolic function of a left and/or right ventricles of a heart, comprising
    attaching an air-impermeable sheet to an external surface of the left ventricle, right ventricle or both ventricles, said air-impermeable sheet is curved or angled to encompass a volume of space,
    ascertaining that air-tight sealing of a peripheral margin of said sheet to an external ventricular wall has occurred, such that an outward and normally directed force may be exerted on the external ventricular surface of the heart due to changes in the volume of said space during the course of a cardiac cycle of said heart, and optionally, as required,
    draining fluid and solid debris from the space formed between one surface of said sheet and the external ventricular wall through drainage means fitted in said sheet to a region located on the other side of said sheet.

7. The method according to claim 6, wherein the drainage means comprises a one-way valve connected to one or more tubes.

8. The method according to claim 6, wherein the air-impermeable sheet is attached to the external ventricular wall during the end of a diastolic period of a cardiac cycle.

9. The method according to claim 6, wherein the air-impermeable sheet is attached to the external ventricular wall by means of one or more attachment means selected from the group consisting of transmural biocompatible pins, other non-transmural pins, biocompatible needles, biocompatible spikes, biocompatible helical coil screws, biocompatible clamps, biocompatible tubes biocompatible glue and surgical sutures.

10. The method according to claim 6, wherein the air-impermeable sheet is attached to the external ventricular wall by means of a fabric patch girdle.

11. The method according to claim 6, wherein the air-impermeable sheet is constructed such that expansive pressure is created due to the outward and normally directed force exerted on at least one part of the external ventricular wall, said expansive pressure having a maximal value in a range of about 5 mm Hg to about 40 mm Hg.

12. The method according to claim 6, wherein the left ventricle of the heart is treated.

* * * * *